(12) United States Patent
Ishitani et al.

(10) Patent No.: US 7,928,377 B2
(45) Date of Patent: Apr. 19, 2011

(54) CHARGED PARTICLE BEAM APPARATUS AND SAMPLE MANUFACTURING METHOD

(75) Inventors: Tohru Ishitani, Hitachinaka (JP);
Tsuyoshi Ohnishi, Hitachinaka (JP);
Mitsugu Sato, Hitachinaka (JP);
Koichiro Takeuchi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 237 days.

(21) Appl. No.: 11/258,035

(22) Filed: Oct. 26, 2005

(65) Prior Publication Data

US 2006/0097166 A1 May 11, 2006

(30) Foreign Application Priority Data

Oct. 27, 2004 (JP) ................................. 2004-312703

(51) Int. Cl.
*G01N 23/04* (2006.01)
(52) U.S. Cl. ......................... 250/306; 250/309; 250/310
(58) Field of Classification Search ................... 250/306
See application file for complete search history.

(56) References Cited

U.S. PATENT DOCUMENTS

| | | | | |
|---|---|---|---|---|
| 3,626,184 | A | * 12/1971 | Crewe | ............................ 250/311 |
| 5,525,806 | A | * 6/1996 | Iwasaki et al. | ........... 250/492.21 |
| 5,616,921 | A | * 4/1997 | Talbot et al. | ...................... 850/9 |
| 5,952,658 | A | 9/1999 | Shimase et al. | |
| 5,986,264 | A | * 11/1999 | Grunewald | .................... 250/310 |
| 6,039,000 | A | * 3/2000 | Libby et al. | ............... 118/723 E |
| 6,452,172 | B1 | 9/2002 | Oi | |

FOREIGN PATENT DOCUMENTS

| | | |
|---|---|---|
| JP | 63-18763 | 2/1988 |
| JP | 6-231719 | 8/1994 |
| JP | 6-231720 | 8/1994 |
| JP | 6-231720 A | 8/1994 |
| JP | 7-92062 | 4/1995 |
| JP | 8-5528 | 1/1996 |
| JP | 9-283496 A | 10/1997 |
| JP | 11-329331 A | 11/1999 |
| JP | 2000-21346 A | 1/2000 |
| JP | 2000-036276 A | 2/2000 |
| JP | 2001-084951 A | 3/2001 |
| JP | 2002-29874 A | 1/2002 |
| JP | 2002-298774 A | 10/2002 |
| JP | 2003-142021 A | 5/2003 |
| JP | 2004-228076 A | 8/2004 |
| WO | WO 99/05506 | 2/1999 |

OTHER PUBLICATIONS

U.S. Appl. No. 11/189,901, filed Jul. 27, 2005, Koichiro Takeuchi, et al.
Japanese Office Action issued in Japanese Patent Application No. JP 2004-312703 dated May 19, 2009.

* cited by examiner

*Primary Examiner* — Phillip A Johnston
(74) *Attorney, Agent, or Firm* — McDermott Will & Emery LLP

(57) ABSTRACT

It is possible to carry out a highly accurate thin film machining by irradiation of an ion beam to a sample and a high-resolution STEM observation of the sample by irradiating an electron beam with a high throughput almost without moving the sample. The FIB irradiation system has an irradiation axis almost orthogonally intersecting an irradiation axis of the STEM observation electron beam irradiation system. The sample is arranged at the intersection point of the irradiation axes. The FIB machining plane of the sample is extracted from the thin film plane of the STEM observation sample. The transmitting/scattered beam detector are arranged at backward of the sample on the electron beam irradiation axis viewed from the electron beam irradiation direction.

13 Claims, 9 Drawing Sheets

DISTANCE ON ION OPTICAL AXIS FROM SAMPLE (mm)

CHARGED PARTICLE BEAM APPARATUS AND SAMPLE MANUFACTURING METHOD

BACKGROUND OF THE INVENTION

1. Field of the Invention

The present invention relates to a charged particle beam apparatus enabling a user to observe the micro-sample extracted from, for example, a semiconductor device substrate while performing micro-machining and a sample fabrication method using the charged particle beam apparatus.

2. Description of the Related Art

The technique of micro-machining using a focused ion beam (FIB) is disclosed, for example, in WO099/05506. By applying an FIB to a sample, it is possible to perform micro-machining using the sputtering phenomenon. Accordingly, it is possible to extract a micro-sample, for example, from a semiconductor device substrate. Moreover, by introducing a deposition gas into the vicinity of the FIB irradiation of the sample and performing the FIB irradiation in the gas atmosphere, a deposition film is formed by the ion beam assisted deposition phenomenon. This film formation can be used for a type of micro-bonding. By installing a probe for lifting out a micro-sample in an FIB sample chamber having a deposition gas supply source, it is possible to fix a micro-sample extracted by the FIB machining to the probe by the FIB deposition film formation, separate it from the sample substrate, and lift out it. The lifted out micro-sample can be fixed to a micro-sample holding unit pre-arranged in the vicinity of the sample substrate in the same sample chamber. The micro-sample holding unit has a shape facilitating its mounting on a sample holder of a transmission electron microscope (TEM) or a scanning transmission electron microscope (STEM) from the viewpoint of operability.

The technique concerning the combination of the FIB apparatus and the STEM is disclosed in JP-A-2004-228076 and JP-A-2002-29874. JP-A-2004-228076 shows that the sample for observation by using the STEM fabricated by the FIB machining is placed at the intersection of the ion beam axis and the electron beam axis and can be additionally machined by the FIB and observed by the STEM. The thin film surface of the STEM sample should be placed almost parallel for additional machining by the FIB and almost vertically for the observation by the STEM. However, according to this technique, the ion beam axis intersects the electron beam axis at an acute angle (about 45 degrees in FIG. 5) and the STEM sample should be rotated around the rotation axis vertical to the both axes between the FIB additional machining and the STEM observation. Moreover, JP-A-2002-29874 also shows an example of intersection of the ion beam axis and the electron beam axis at an acute angle (about 50 degrees in FIG. 1).

On the other hand, JP-A-6-231720 discloses a technique concerning fabrication of a TEM sample. In this technique, in order to check the film thickness of the TEM sample to be thin-film-machined by the FIB, an electron beam is applied in vertical direction with respect to the cross section of the sample so as to detect an intensity ratio between the electron beam irradiation intensity and the electron beam which has transmitted through the sample. Here, the transmitted electron beam does not distinguish detection of a transmitted beam having a very small scattering angle as an STEM signal from the scattered beam which has transmitted and scattered and the sample film thickness is not monitored from the STEM observation point. The similar technique is also disclosed in JP-8-5528. Moreover, JP-A-6-231719 discloses an apparatus characterized in that a FIB irradiation system is arranged in the vertical direction with respect to the TEM electron beam axis in the sample chamber of the TEM apparatus and the TEM sample fabricated by the FIB machining can be directly observed by the TEM without extracting the TEM sample into the atmosphere, thereby solving the problem of a low throughput during the FIB additional machining. JP-A-6-231719 also discloses a TEM image monitor as control of the sample film thickness.

Moreover, JP-A-7-92062 discloses an example of the in-situ TEM observation of a sample being subjected to FIB machining. However, since the FIB is introduced not vertical to the sample surface, there is a defect that a beam damage is made deeper as compared to the cross section thin film sample which is fabricated almost parallel to the FIB incident axis.

As for the STEM single apparatus, it is disclosed, for example, in JP-A-2000-21346. The beam scan image detecting a transmitted electron from the sample for use as a brightness signal is called a bright field image while the beam scan image detecting a scattered electron for use as a brightness signal is called a dark field image. The contrast of the bright field image reflects absorption, diffraction, and phase shift of the irradiated electron in the sample. On the other hand, the dark field image uses only the diffracted electron, which is reflected in a particular angle direction, for use as a brightness signal and the size of the crystal grain is clearly appears. The bright field image and the dark field image are both images (STEM images) formed by the beam which has transmitted through the sample and very helpful for analysis of the thin film structure.

Moreover, the irradiated electron beam of the STEM apparatus conventionally has a high energy in the order of 200 keV like the TEM. However, recently, the STEM observation is performed in the energy region of 30 keV like the conventional SEM as reported in Journal Electron Microscopy 51(1):53-57(2002). When the electron beam irradiation energy is lowered, the transmission capability of the thin film sample is also lowered. Accordingly, in the low-energy STEM apparatus, a highly accurate film thickness management is normally required for the thin film sample fabricated by the FIB machining.

SUMMARY OF THE INVENTION

However, the FIB machining and the STEM observation have been performed conventionally by different apparatuses in may cases. The STEM thin film sample machined/manufactured by the FIB apparatus is taken out from the FIB apparatus and then placed in the STEM apparatus for observation. For this, it has been impossible to satisfy the needs of thin film formation performed at high throughput while further specifying an observation point by repeating the STEM observation and the FIB additional machining. Recently, an apparatus for performing the FIB processing and the STEM observation has been developed. However, there remains an operation work for rotating the sample between the FIB machining stage and the STEM observation stage so as to match the sample thin film surface with the respective directions.

From the viewpoint of the STEM image observation, it is important to assure a sufficiently strong image signal and a high contrast but normally they cannot be satisfied simultaneously (they are incompatible). Especially in the dark field image, the optimal sample thickness varies, depending on the sample material (atomic number), the observation part, uniformity in the thickness direction in the sample boundary of the observation object, and the like. Accordingly, it is difficult to estimate the optimal sample thickness in advance. For this, it is necessary to gradually reduce the sample film thickness toward the optimal thickness from the thicker direction while monitoring the STEM image during the machining.

The first object to be achieved by the present invention is to provide an apparatus capable of realizing the FIB machining and the STEM observation in a single sample chamber with a high throughput by eliminating (or minimizing) the sample rotation work between ten FIB machining stage and the STEM observation stage and simplifying the work for optimizing the sample thickness by using the STEM image monitor in the middle of machining.

On the other hand, in the STEM observation with a low energy (in the order of 30 keV), the image resolution is lowered for the thickening of the beam diameter as compared to the STEM observation with a high energy (in the order of 200 keV). Here, some users want to increase the image resolution of the STEM observation even by sacrificing the simplicity of the work operation and the throughput to a certain extent. The second object is to provide a device having a sufficient STEM image resolution.

In order to achieve the first object, it is necessary to arrange the ion beam irradiation system, the electron beam irradiation system, and the transmitting/scattered beam detection means in the vicinity of a sample so that the sample need not be moved for both of the FIB machining and the STEM observation. That is, the irradiation axis of the FIB irradiation system intersects the irradiation axis of the electron beam irradiation system for the STEM observation almost orthogonally and the sample is placed at the intersecting point so that the FIB cross section machining surface of the sample is defined by the thin film surface of the sample for the STEM observation. Moreover, the transmitted/scattered beam detection means is arranged backward of the sample viewed from the electron beam irradiation direction on the electron beam irradiation axis. By this arrangement, it is possible to realize the FIB machining and the STEM observation almost without moving the sample.

Next, explanation will be given on the means for achieving the aforementioned second object. From the first viewpoint for eliminating (or minimizing) the work such as a sample rotation work between the FIB machining stage and the STEM observation stage and simplifying the sample thickness optimization work using the STEM image monitor in the middle of the machining, the irradiation axis of the FIB irradiation system intersects the irradiation axis of the electron beam irradiation system for the STEM observation almost orthogonally. On the other hand, from the viewpoint for reducing the beam diameter in the FIB machining (high-speed machining and high machining position accuracy) and increasing the resolution of the STEM observation, the objective lenses of the electron beam irradiation system and the ion beam irradiation system should be arranged in the vicinity of the sample. However, because of the spatial size of the objective lenses of the both irradiation systems, the distance near the sample is limited. Under the condition to increase the image resolution of the STEM observation even by sacrificing the simplicity of the work operation and the throughput to a certain extent, if is effective that the irradiation axis of the FIB irradiation system and the irradiation axis of the electron beam irradiation system for the STEM observation intersect each other at an angle exceeding the right angle. With this arrangement, it is possible to arrange the objective lens of the electron beam irradiation system nearer to the sample as compared to the case when the irradiation axis of the FIB irradiation system and the irradiation axis of the electron beam irradiation system for the STEM observation intersect each other almost at a right angle.

When the objective lens of the electron beam irradiation system is a magnetic field type lens, by leaking the magnetic field toward the sample side, the objective lens can substantially approach the sample. This can also serve as means for achieving the high performance of the STEM observation. When the FIB is formed by isotope ion, the leakage magnetic field separates the ion beam orbit in the magnetic field, which in turn causes separation at the beam irradiation point on the sample. This problem can be solved by forming a compensation magnetic field so that the separated beams are again focused to a point on the sample.

According to the present invention, it is possible to realize a FIB machining for fabricating a thin film sample by a higher micro-machining performance and a STEM observation for the STEM observation with a higher resolution. Moreover, in the thin film sample, it is possible to regulate the film thickness with a high accuracy. Thus, it is possible to realize the FIB machining to the STEM observation in the time series or simultaneously in a single sample chamber with a high throughput.

Other objects, features and advantages of the invention will become apparent from the following description of the embodiments of the invention taken in conjunction with the accompanying drawings.

DESCRIPTION OF THE EMBODIMENTS

Description will now be directed embodiments of the present invention with reference to the attached drawings.

First Embodiment

Figure 1:
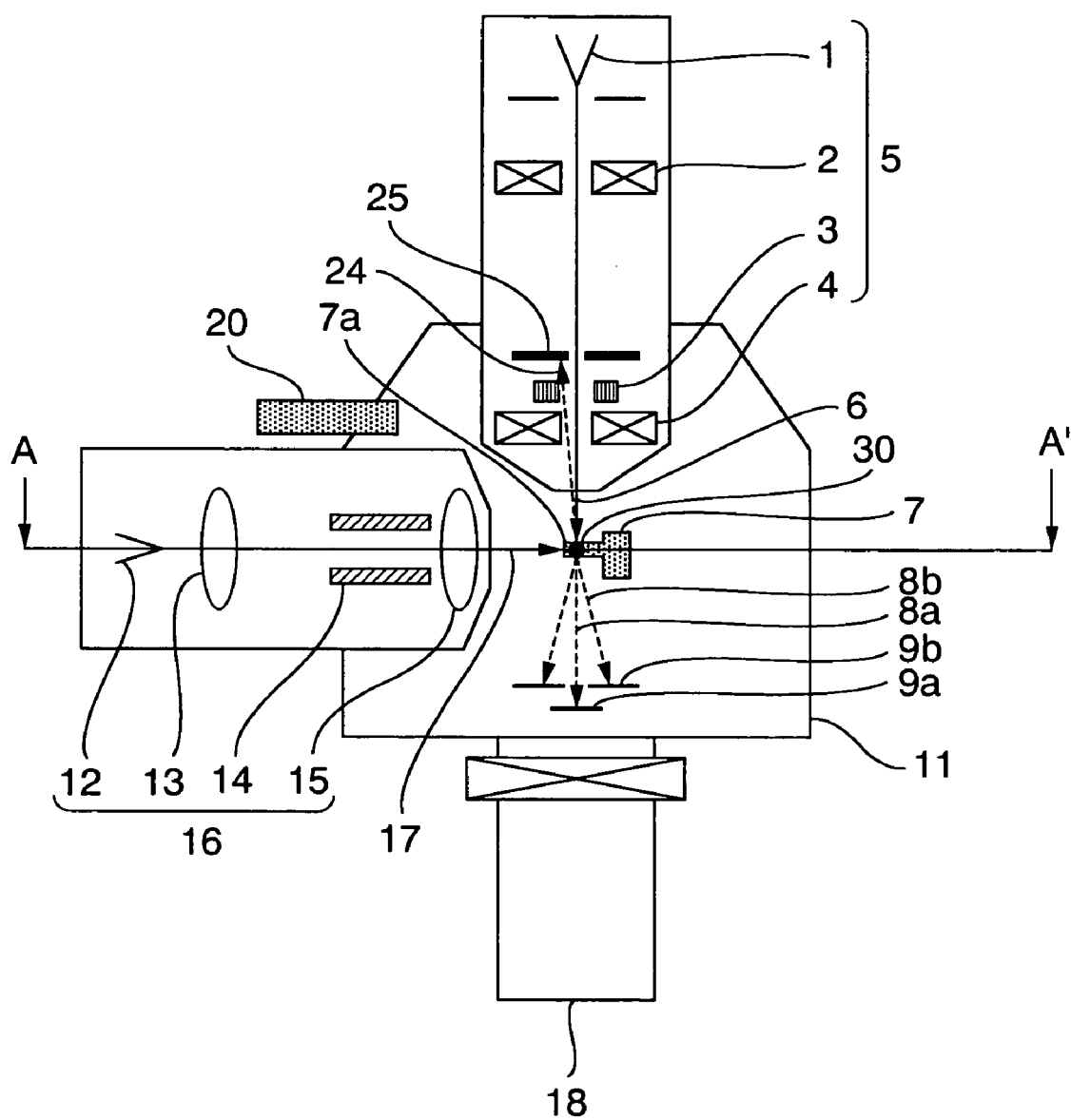
FIG. 1 shows a brief configuration of charged particle beam apparatus according to a first embodiment of the present invention.
Figure 2:
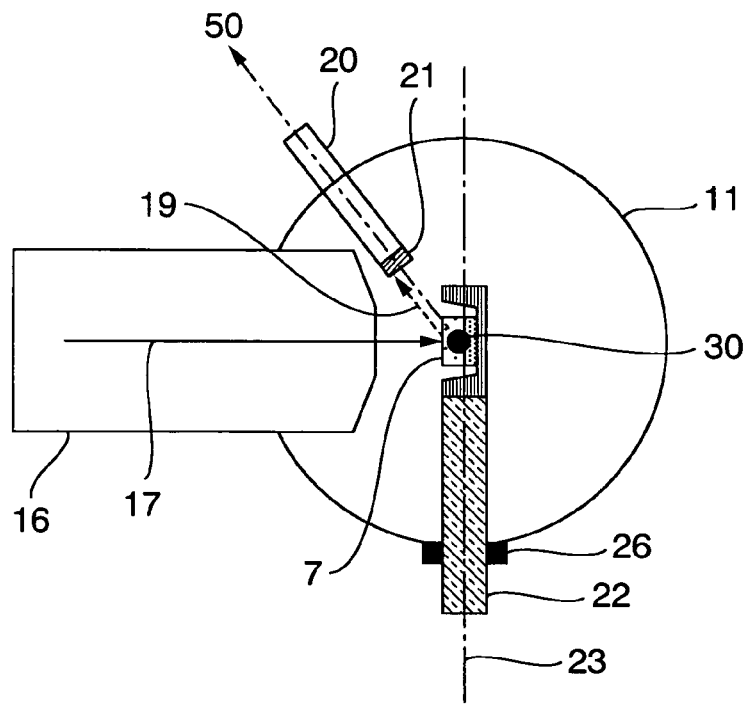
FIG. 2 is a cross-sectional view of FIG. 1 about A-A'.

FIG. 1 shows a brief configuration of a charged particle beam apparatus according to the first embodiment of the present invention. FIG. 2 is a cross sectional view of FIG. 1 about A-A'.

The electron beam irradiation system 5 and the ion beam irradiation system 16 are mounted on a sample chamber case 11 so as to irradiate a sample 7. The electron beam irradiation system 5 includes a focusing lens 2 for focussing the electrons emitted from an electron gun 1, an electron beam deflector 3, and an objective lens 4 and has a function of irradiation of an electron beam 6 onto the sample 7 while reducing the beam diameter to a sufficiently small value and performing scan. On the other hand, the ion irradiation system 16 includes a focusing lens 13 for focusing ion emitted from the ion gun 12, an ion beam deflector 14, and an objective lens 15 and has a function of irradiation of a focused ion beam (FIB) onto the sample 7 while reducing the beam diameter to a sufficiently small value and performing scan of a particular range of a particular portion. In the embodiment of FIG. 1, the irradiation axes of the electron beam 6 and the ion beam 7 onto the sample 7 almost intersect each other and the intersection angle is almost a right angle (=90 degrees±1 degree). The sample is placed on the intersection point 30 and the thin film machining by the ion beam irradiation and the STEM observation by the electron beam can be carried out with a preferable operability almost without moving the sample.

A part of the sample is made into a thin piece by the FIB machining and the electron beam 6 irradiates/scans on the thin piece 7a. The transmitting beam 8a which has passed through the thin film part 7a and the scattered beam 8b are detected by the transmitting beam detector 9a and the scattered beam detector 9b, respectively. In addition to this, there are secondary electron detection means 20 and reflective electron detection means 25. The secondary electron detection means 20 detects the secondary electrons 19 emitted from the sample 7 during the FIB machining. In FIG. 1, the secondary electron detection means 20 is located actually backward of the ion beam irradiation system 16 and cannot be seen. Accordingly, for convenience, it is drawn immediately above the ion beam irradiation system 16. Actually, as shown in FIG. 2 showing the cross section about A-A' (plane vertical to the irradiation axis of the electron beam 6 and including the irradiation axis of the ion beam 17), the secondary electron detection means 20 is arranged in the cross section A-A'.

Figure 3:
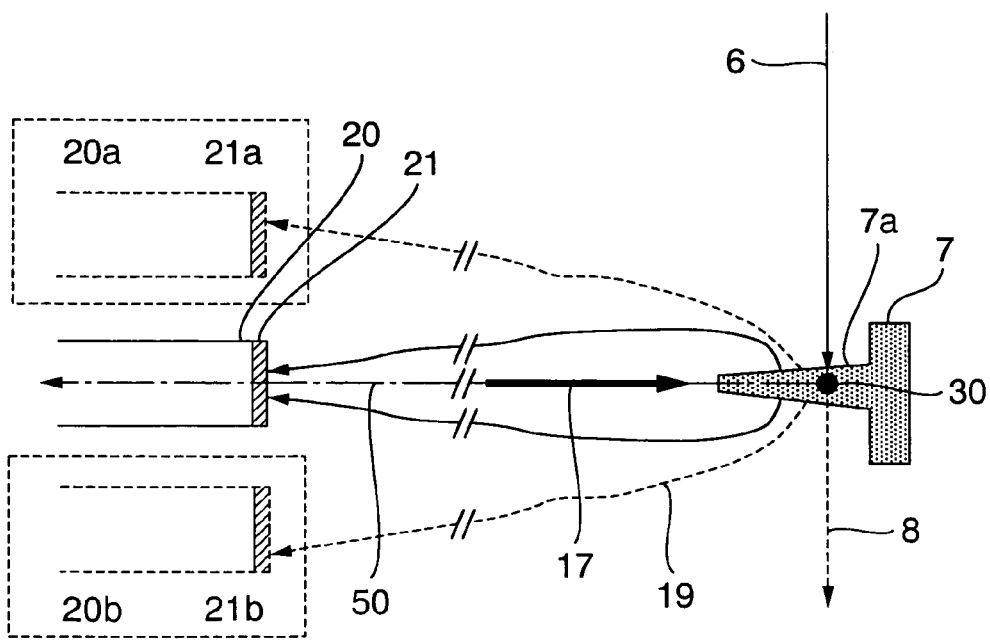
FIG. 3 explains a layout of the secondary electron detection surface in the cross section including the rectilinear axis drawn from the sample to the secondary electron detection surface and the electron beam irradiation axis.

When the straight line drawn from sample 7 to the secondary electron detection means 20 is the axis 50, the axis is in the plane of the cross section A-A'. FIG. 3 is a cross sectional view including the axis 50 and the irradiation axis of the electron beam 6. The secondary electron detection means 20 has a secondary electron entering plane 21 whose center is on the axis 50. That is, the secondary electron entering plane 21 is arranged at a position almost symmetric with respect to the plane including the axis 50 and the irradiation axis of the ion beam 17. Accordingly, during the machining of the front surface and the rear surface of the thin film sample 7a by the FIB, it is possible to collect and detect the secondary electrons 19 emitted from the respective surfaces almost with identical yield. The scan image is called a scan ion microscopic image (SIM image). A sample holder 22 has a holder axis 23 which is vertical to the both irradiation axes of the electron beam and the ion beam and on the axis passing through the intersection point 30 of the both irradiation axes. The sample holder 22 is held on a sample stage 26 for moving the or tilting the sample in job mode. The sample stage 26 is fixed to the sample chamber case 11.

Explanation has been given on a case that one secondary electron detection plane is used. However, in order to increase the secondary electron collection efficiency, it is also possible to use two planes as shown by the symbols 21a and 21b in the rectangular shapes drawn by broken lines in FIG. 3. In such a case also, like the aforementioned, the secondary electron entering plane should be arranged at the position almost symmetric with respect to the plane including the axis 50 and the irradiation axis of the ion beam 17. Moreover, this secondary electron detection means 20 is also used when detecting secondary electrons 19 emitted from the sample 7 when the electron beam is irradiated. Especially when two(or a plurality of) secondary electron entering planes are arranged almost symmetric with respect to the plane as shown by the broken lines in FIG. 3, it is possible to perform detection while separating the secondary electrons generated from the front surface from the secondary electrons generated from the rear surface of the thin film sample. When the electron beam is irradiated, in addition to the secondary electrons from the sample 7, reflected electrons 24 reflected backward are also generated. For this, reflected electron detection means 25 is also provided for detecting the reflected electrons 24 (see FIG. 1). All the detection signals can be used as brightness signals of the scan image drawn in synchronization with the beam scan signal.

Figure 4:
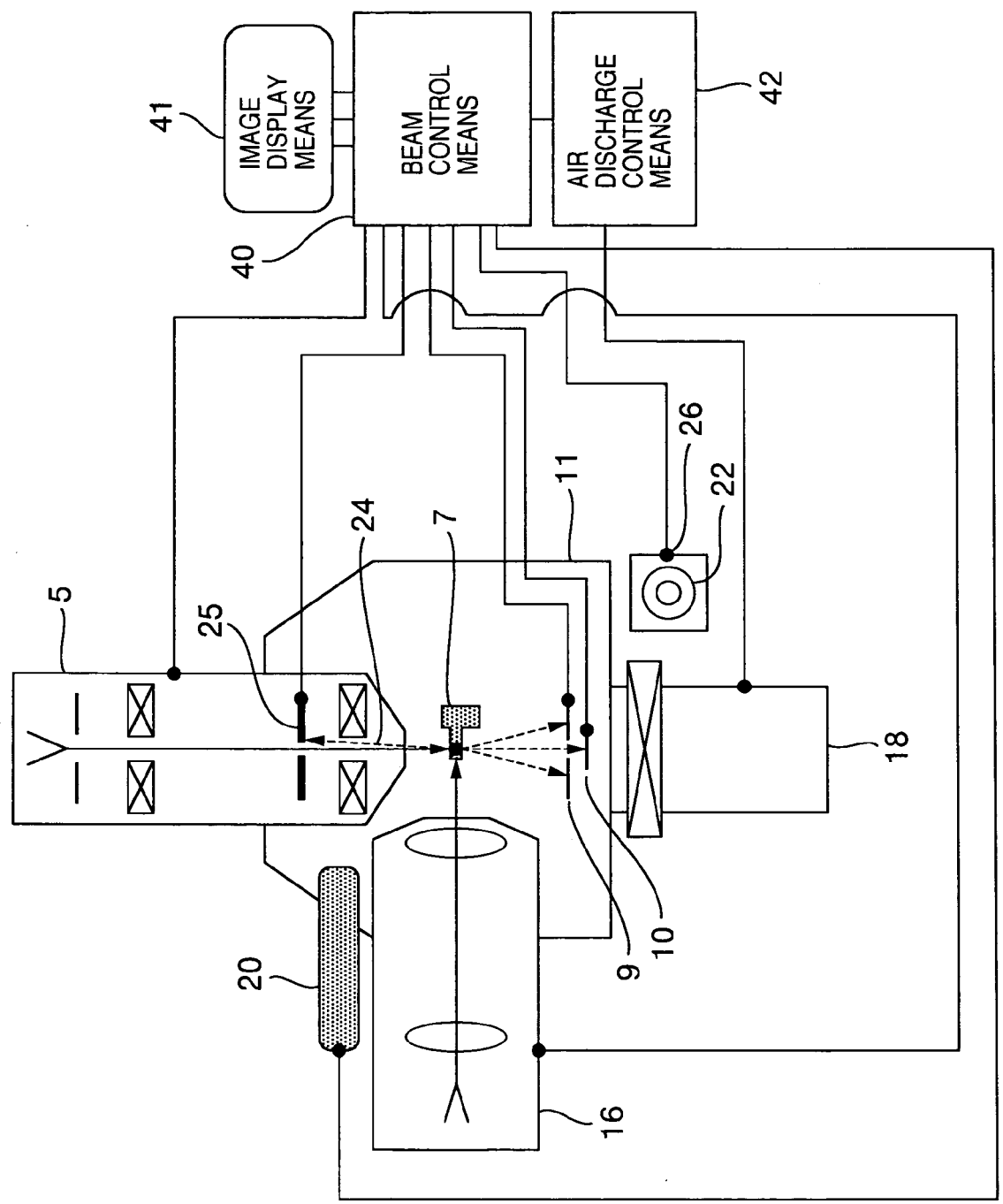
FIG. 4 shows the entire configuration including a beam irradiation system, a beam control unit, and image display means according to the present invention.

FIG. 4 is a block diagram showing the entire configuration of the charged particle beam apparatus according to the present invention including a beam irradiation system, a beam control unit, and image display means. In FIG. 4, all the detection signals from the detection means are taken into the beam control means 40. Moreover, beam control of the electron beam irradiation means 5 and the ion beam irradiation means 16 is performed from the beam control means 40. The beam control means 40 includes a voltage/current source for applying voltage and current to the beam irradiation means and a computer which performs software processing such as voltage/current control and processing of signals from the respective detectors. Moreover, The beam control means 40 is electrically connected to image display means 41 for input/output and display of parameters for the control and processing and displaying various scan images. Moreover, for the various scan images, the image average brightness, contrast, signal noise ratio (S/N ratio), and image resolution are numerically evaluated and can be displayed in numerical values or in a graph in the display screen of the image display means 41. Generally, as the thin film sample becomes thinner, the transmitting electron beam amount increases and accordingly, the brightness increases and the image resolution is improved (the resolution value becomes smaller).

Figure 5A:
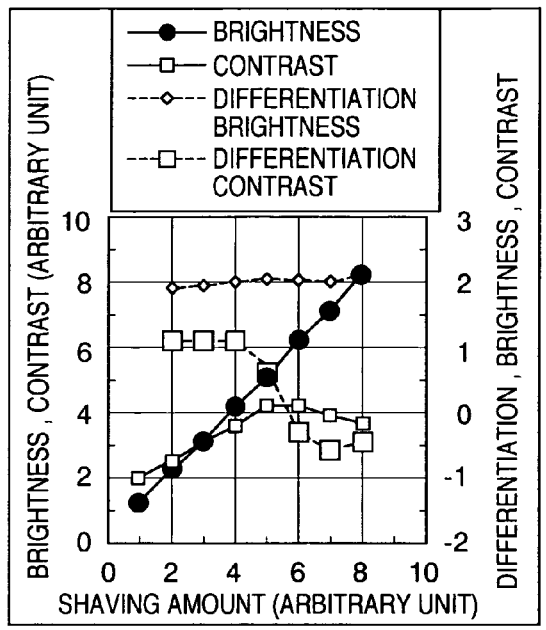
FIG. 5A shows an example of a graph displaying brightness and contrast in the bright field image with respect to a shaving thickness (arbitrary unit) when finishing the sample by the FIB.
Figure 5B:
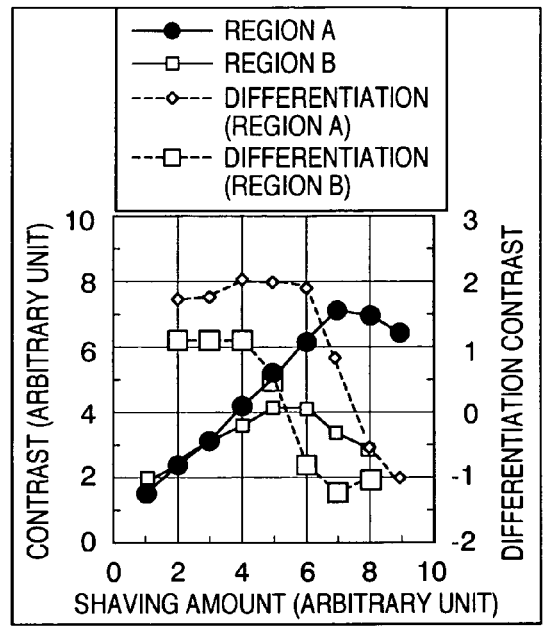
FIG. 5B shows an example of a graph displaying the shaving thickness (arbitrary unit) of the contrast in the region including the boundary A and B in the dark field image.

FIG. 5A shows an example of a graph displaying the brightness and the contrast in the bright field image of STEM with respect to the shaving thickness (arbitrary unit) when finishing the sample by the FIB. FIG. 5B shows an example of a graph displaying the shaving thickness (arbitrary unit) of the contrast in the region including the boundary A and B in the dark field image. The brightness and the contrast represent values of average brightness in the rough scan image (512× 512 pixels) and a brightness range of 10% to 90% of the pixel brightness histogram which is divided by the average brightness. The brightness and the contrast are calculated in real time at a predetermined timing from the STEM image obtained during machining and the calculation results are successively added and plotted in the graph.

In the bright field image, as the sample becomes thinner, the brightness and the contrast increase as shown in FIG. 5A. However, the contrast is saturated in the middle and tends to decrease. The cause of the saturation of the contrast in the middle and the tendency to decrease from the middle is not known. In the contrast of the dark field image shown in FIG. 5B, it is known that the saving amount which brings about the maximum contrast is different between the boundary area A and B to be observed. That is, when observing a particular boundary region with a high contrast of the dark field image, the optimal sample thickness cannot be known even by monitoring the all the beam intensity transmitting through the sample. It is necessary to acquire the actual dark field image and monitor the contrast while gradually reducing the sample thickness. After reaching the optimal sample thickness, the highly accurate target STEM image (1024×1024, 2048×2048, 4096×4096 pixels) was acquired.

In addition to the brightness and the contrast of the scan image, it is possible to display the S/N ratio and the image resolution in graph (or numerical values). In order to clearly shows the change of the curve, the display graph has mode for displaying the differential curve for the shaving amount. In the aforementioned FIG. 5A and FIG. 5B, in addition to the plotting of the brightness and the contrast with respect to the shaving amount, its differentiation amount (arbitrary unit) is also plotted on the right vertical axis. The intersection point with the line of y=0 of the differentiation plot curve corresponds to the maximum value of the original plot curve before differentiation and the differentiation plot curve is helpful for grasping the condition reaching the maximum value. In the graph plot display, it is possible to select the original plot or the superposition of the original plot and the differentiation plot.

Hereinafter, explanation will be given on the calculation method used in this embodiment for the brightness, the contrast, the S/N ratio, and the image resolution. There is still no method established for evaluating these from the original image and the method is being studied and developed. Firstly, the brightness is a value obtained by subtracting the origin (the pixel intensity average value when the beam irradiation is stopped) from the average value of the pixel intensity in a particular area within the image specified by the image observer. The contrast is a strength difference between 90% at maximum and 10% at minimum in the histogram of the image intensity of a particular area. As for the S/N ratio and the image resolution, the image evaluation method disclosed in JP-A-2003-142021 was used. That is, for each pixel position of the image, a local xy area 3×3 around the position is isolated and by using the pixel intensity there as z, the secondary curved surface expressed by the expression below is fitted (thereby deciding the coefficients a to f).

$$z=ax^2+by^2+cxy+dx+ey+f \text{ ($a$ to $f$ are coefficients)}$$

The fitting is shifted greatly if the image noise is large. The average of the fitting shift in an entire particular area is made N of the S/N ratio and the aforementioned brightness is made S, so that the ratio of the S and N (=S/N) is used as the S/N ratio. As for the image resolution, the reciprocal of the gradient at the center of the secondary curved surface attached to the aforementioned local xy area 3×3 is made a proportion amount of the local image resolution and the weighted average of the proportion amount in the entire particular area is made the image resolution (arbitrary unit). The absolute value of the gradient is used as the weight.

The graph display of the brightness, the contrast, the S/N ratio, and image resolution is performed while actually observing the STEM image. This is very helpful for making a judgment whether to continue or stop the FIB machining or to perform additional machining or not while paying attention to allover situation or a particular image evaluation parameter (brightness, contrast, S/N ratio, image resolution, and the like). Especially from the viewpoint of the automatic machining, it is possible to register thresholds of features (brightness, contrast, S/N ratio, image resolution, and the like) of the desired STEM image before fabrication of a thin film sample by the rough FIB machining, thereby enabling automatic machining. The beam control means 40 can have the function to register the thresholds of the brightness, the contrast, the S/N ratio, or the image resolution, the function to decide whether the feature of the STEM image has reached the threshold registered in advance, and the function to stop the ion beam irradiation and terminate the rough machining when it is judge d that the feature of the STEM image has reached the threshold registered in advance.

Figure 6:
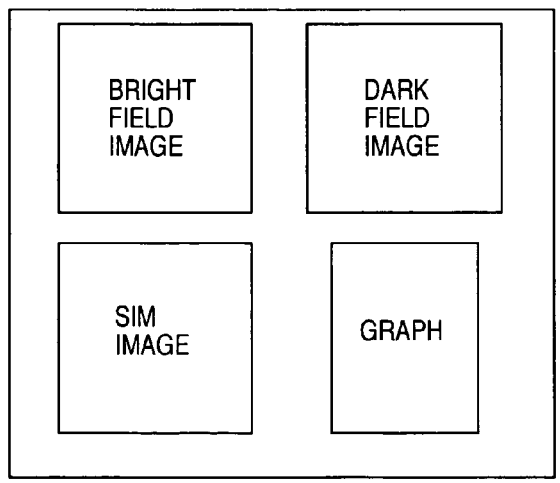
FIG. 6 shows a bright field image, a dark field image, a SIM image, and a display graph arranged in a display frame of the image display means.

FIG. 6 shows an example of layout of the bright field image, the dark field image, the SIM image, and the aforementioned display graph displayed in a display frame of the image display means 41.

Hereinafter, the method how to use the scan image will be summarized. The SIM image is used for setting the FIB machining position, machining monitor during machining, check upon completion of the machining, observation of the cross section, and the like. On the other hand, the signals obtained by the electron beam irradiation are secondary electron, reflected electron, transmitting electron, and scattered electron and their scan images are called a secondary electron image, a reflected electron image, a bright field image, and a dark field image, respectively. The first two images are the SEM images and the remaining two images are the STEM images. The STEM image is formed by the beam which has transmitted through the sample and very helpful for analysis of the thin film structure. Moreover, since the ion irradiation axis and the electron beam irradiation axis intersect each other at 90 degrees, it is possible to observe the sample being subjected to the FIB machining from the lateral direction by the SEM. In the thin film sample fabricated by the SEM cross section machining, its top portion may be etching-damaged by the FIB beam bottom. The SEM image is very helpful for monitoring/observing the etching damage. Moreover, there is no need of moving the sample between the FIB machining and the STEM observation. A combined observation of the SIm image, the SEM image, and the STEM image are very effective from the viewpoint of operability, throughput, and the quality of the observed image especially when tracing the detailed analysis portion by the FIB machining while looking at the observation image. The STEM image (or the SEM image) observation and the FIB machining can be performed in time series or simultaneously. Thus, an operator monitoring the scan image can always interrupt or resume the FIB machining, thereby realizing a highly accurate machining of a particular part of the sample and the STEM observation of high resolution with a high throughput.

Second Embodiment

Figure 7:
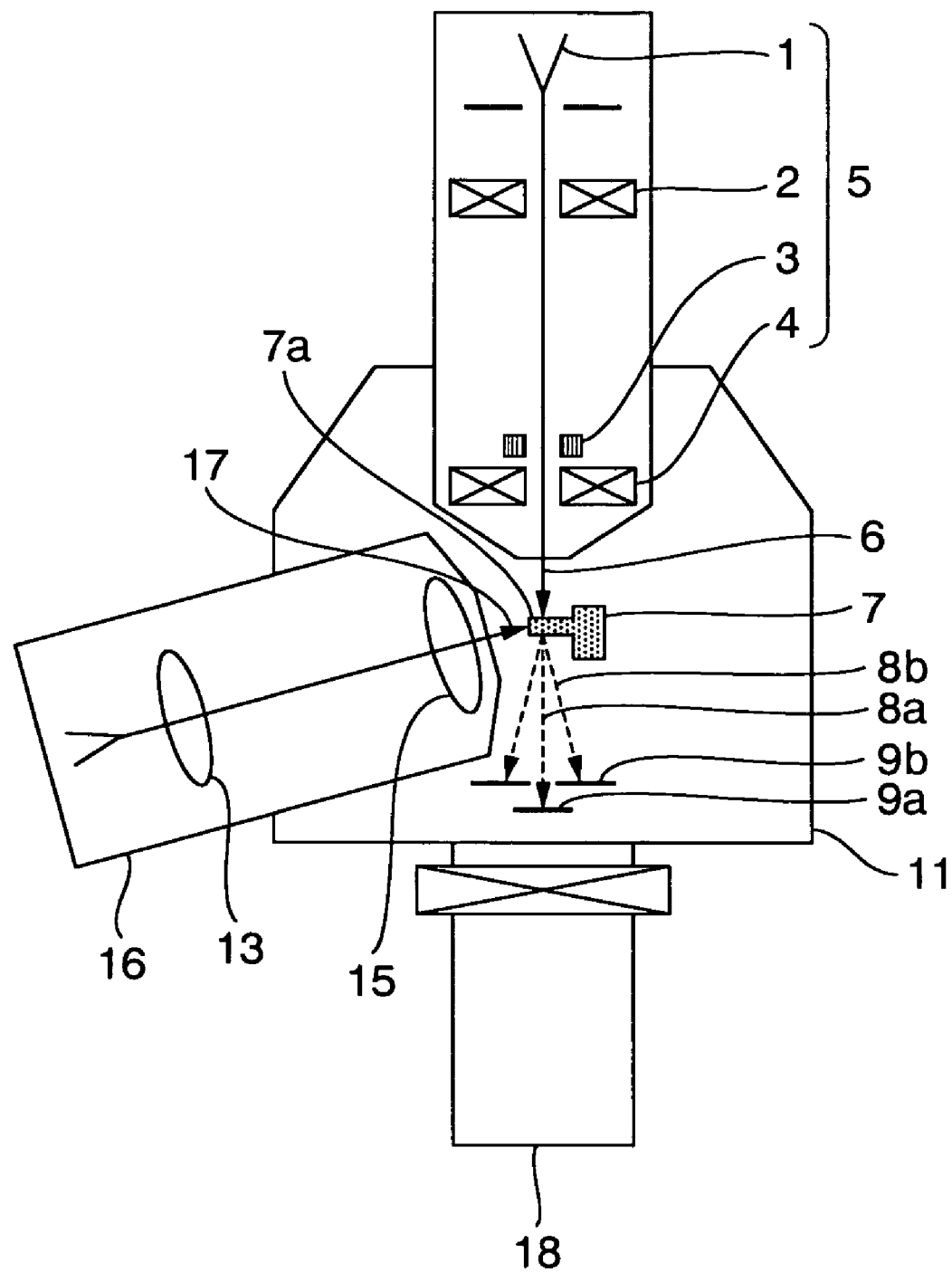
FIG. 7 shows a brief configuration of a charged particle beam apparatus according to a second embodiment of the present invention.
Figure 8:
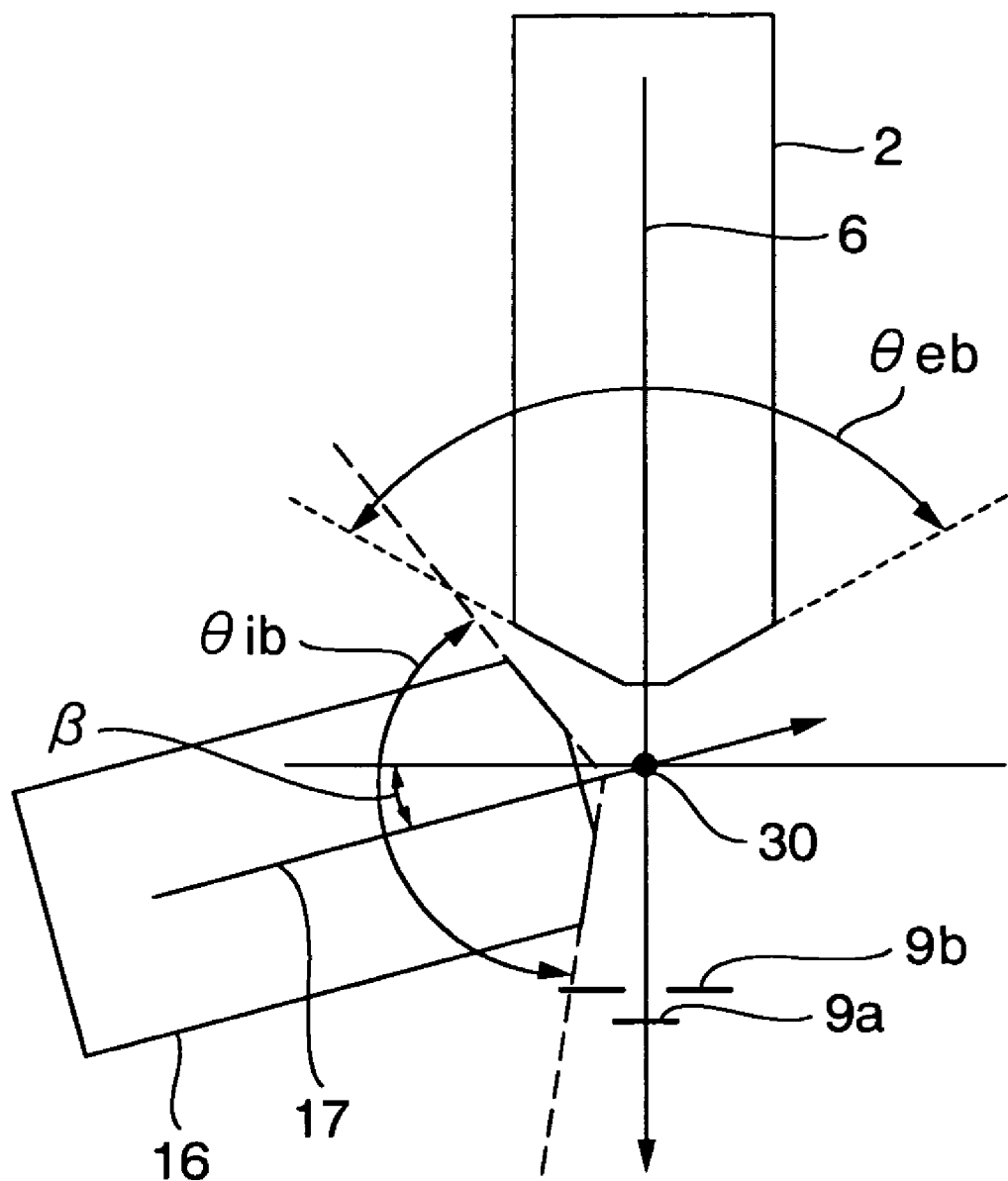
FIG. 8 explains the intersection angle between the electron beam irradiation axis and the ion beam irradiation axis.

FIG. 7 shows a brief configuration of the charted particle beam apparatus according to a second embodiment of the present invention. FIG. 8 explains an intersection angle between the electron beam irradiation axis and the ion beam irradiation axis. The charged particle beam apparatus according to the present embodiment is an example in which the intersection angle between the electron beam irradiation axis and the ion beam irradiation axis exceeds 90 degrees.

In this embodiment the intersection angle between the irradiation axes of the electron beam 6 and the ion beam 17 to the sample 7 is set to 110 degrees. Thus, as compared to the first embodiment in which the intersection angle is 90 degrees, the objective lens 15 of the ion irradiation system 16 can approach the sample by amount 3 mm and the FIB diameter can be reduced by about 15% when the machining beam performance has the same current calculation value. This is equivalent to that the FIB machining position accuracy under the same machining speed condition is improved by about 15%. However, it is necessary to move the sample 7 in the diagonal direction for the sample inclination angle difference β (see FIG. 8) between the FIB machining and the STEM observation. Like in FIG. 2, the sample holder 22 has its holder axis 23 vertical to both of the electron beam and the ion beam irradiation axis and on the axis passing through the intersection point 30 of the irradiation axes so that the sample movement required between the FIB machining and the STEM observation is only the inclination angle of the sample inclination angle difference β. The sample holder 22 is held on the sample stage 26 for micro-movement of the sample including the inclination. The sample stage 26 is fixed to the sample chamber case 11.

Since the objective lens of the electron beam irradiation system and the objective lens of the ion beam irradiation system are arranged in the vicinity of the sample, in order to increase the space of the vicinity of the sample to maximum, the intersection angle of the both beam irradiation axes is preferably 180 degrees. However, in the direction of the 180-degree axis direction from the electron beam irradiation axis, the transmitted/scattered beam detection means 9a and 9b are arranged. Accordingly, the 180 degrees cannot be used. More specifically, considering the circular cone angle θeb of the objective lens side of the electron beam irradiation system 5 and the irradiation system diameter, the circular cone angle θib of the objective lens side of the ion beam irradiation system 16 and the irradiation system diameter, and the size of the transmitted/scattered beam detection means, it is necessary to obtain balance between the movement angle β and the beam performance improvement and the intersection angle between the two beam irradiation axes is set between 90 degrees and 180 degrees.

Third Embodiment

Figure 9:
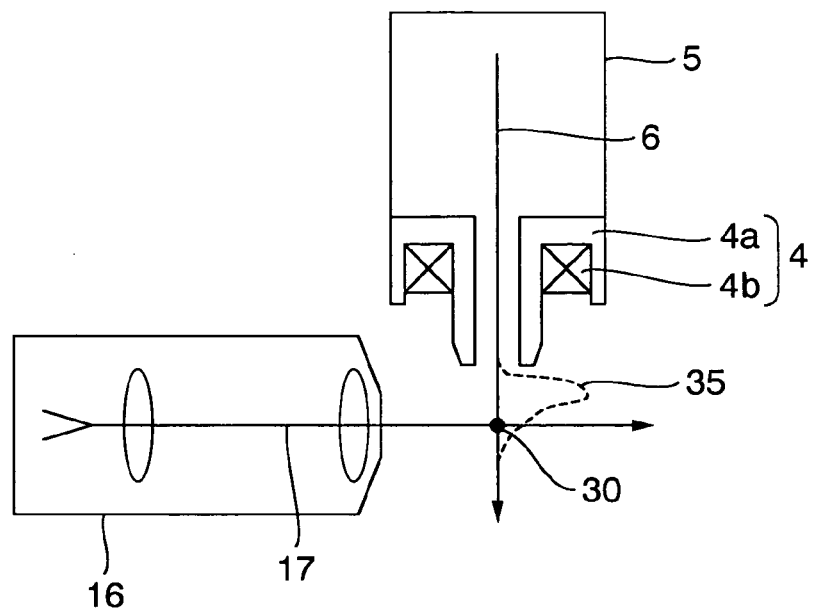
FIG. 9 shows a combination of an ion beam irradiation system and an electron beam irradiation system having an objective lens which is a magnetic field type lens and whose magnetic field is leaked to the sample side.

When the objective lens of the electron beam irradiation system is a magnetic field type lens, the magnetic field is made to leak to the sample side so that the objective lens substantially approaches the sample, thereby increasing the STEM observation performance. The present embodiment is related to the leak magnetic field type objective lens, which will be detailed with reference to FIG. 9.

Figure 10:
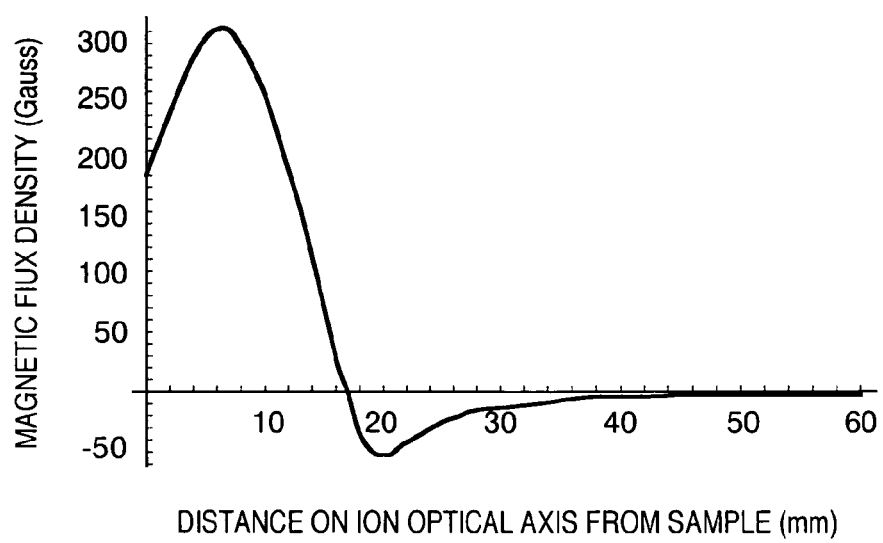
FIG. 10 shows an example of magnetic flux distribution of the magnetic field leaking from the objective lens of the electron beam irradiation system, on the ion beam irradiation axis.

The objective lens 4 is a leak magnetic field type including a magnetic pole piece 4a and an excitation coil 4b. The magnetic field is made to leak to the sample side, i.e., the side of the intersection point 30 between the irradiation axis of the electron beam 6 and the irradiation axis of the ion beam 17 so as to form a magnetic flux density distribution 35 on the irradiation axis of the electron beam 6. The leaking magnetic field exists on the irradiation axis of the ion beam 17, too. FIG. 10 shows the magnetic flux distribution of the ion beam 17 on the irradiation axis. As the ion species of the ion beam for the FIB machining, normally gallium (Ga) is used. Since the Ga has isotopes $Ga^{69}$ and $Ga^{71}$, the magnetic flux distribution on the irradiation axis of the ion beam 17 separates the beam spot on the sample and substantially increases the beam diameter in the separation direction. This beam diameter increase deteriorates the machining position accuracy and its countermeasure is required. For this, the following means has been used.

When magnetic field distribution of the magnetic field type objective lens in the electron beam irradiation system is analyzed in detail, it is known that for example, a downward (or upward) strong magnetic field is present in a narrow region in the vicinity of the electron beam irradiation axis and an upward (or downward) weak magnetic field is present in a wide region outside the objective lens. The ion beam irradiation axis passes through the magnetic field space of the both directions. In order to solve the problem of the ion beam spot separation, the following characteristic is utilized. When regions having magnetic components vertical to the optical axis are in the opposite directions are provided on the ion beam optical axis and as a result, the beam spot position on the sample is matched with case when no magnetic field exists, the ion optical path from the ion gun to the sample differs depending on the isotope but the beam spot position on the sample is matched. More specifically, a cancellation magnetic field generation unit is arranged on the optical axis of the ion beam irradiation axis and the leakage magnetic field is combined with the cancellation magnetic field so that a cancellation magnetic field is set in such a manner that the beam spot position on the sample is matched with the case when no magnetic field exists.

Figure 11:
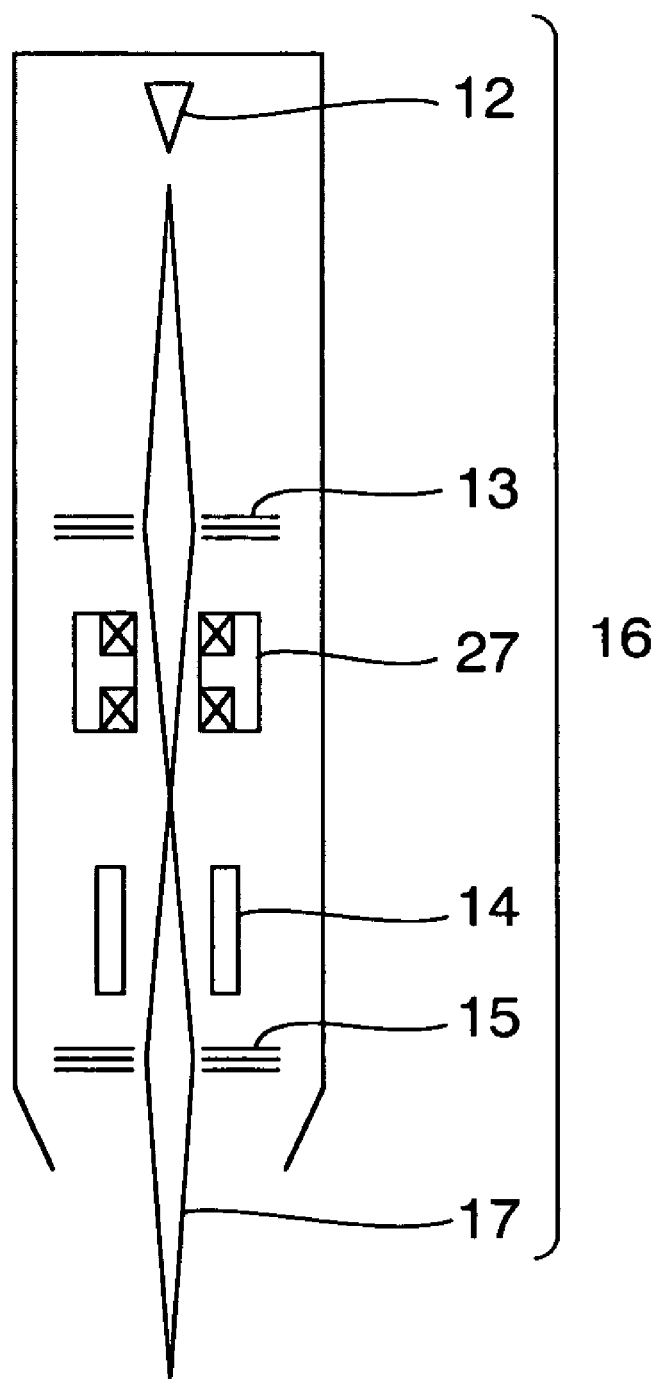
FIG. 11 explains the ion beam irradiation system having a built-in cancellation magnetic field generation unit.
Figure 12A:
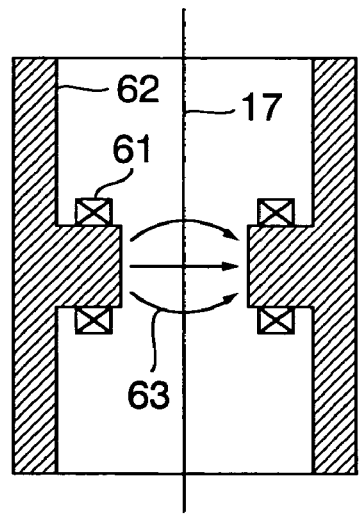
FIG. 12A and FIG. 12B show a brief configuration of the cancellation magnetic field generation unit.
Figure 12B:
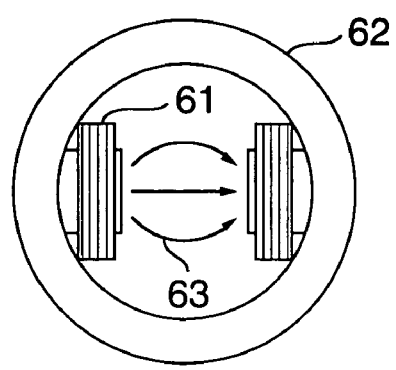

FIG. 11 shows an embodiment of the ion beam irradiation system having a cancellation magnetic field generation unit 27 on the optical axis. FIG. 12A and FIG. 12B show a brief configuration of the cancellation magnetic field generation unit. FIG. 12A is a cross sectional view and FIG. 12B is a top view. The cancellation magnetic field generation unit 27 includes a pair of opposing coils 61 and permalloy magnetic path 62. The magnetic path 62 effectively generates a cancellation magnetic field on the ion beam optical axis and simultaneously with this, serves as a magnetic shielding body suppressing leakage magnetic field from the coils 61 to outside. Here, the material of the magnetic path is not to be limited to permalloy but may be any material having a large permeability and small coercive force such as pure iron and permendur. As the permeability becomes large, it is possible to reduce the leakage magnetic field to outside. The cancellation magnetic field generation unit 27 has a beam passage in the center and the beam passage is arranged to coincide with the irradiation axis of the ion beam 17. The beam passage of the cancellation magnetic field generation unit 27 has a diameter for passing all the ion beams which have passes through the focusing lens 13.

In this Figure, the direction of the cancellation magnetic field 63 generated on the ion beam optical axis is parallel to the paper surface and vertical to the optical axis. In this case, a Lorentz force functions on the ion beam in the direction vertical to the paper surface and the optical axis. This direction is parallel to the Lorentz force generated by the magnetic field from the objective lens 4 of the SEM. By appropriately adjusting the direction and intensity of the cancellation magnetic field, the irradiation spot position of the ion beam on the sample 7 can completely coincide with the position when no magnetic field exists.

Here, the beam spot need not be always circular. The discussion here effective even when the beam cross section is elliptic linear. In this invention, the beam spot includes any shape. The cancellation magnetic field generation unit may be anywhere on the ion beam optical axis. However, it is preferably far enough from the sample 7 so that the magnetic field of the SEM objective lens is not disturbed. Moreover, in the cancellation magnetic field generation unit 27 in FIG. 11, a pair of coils is used for example, but the two or more pairs of coils may also be used. When two or more pairs of coils are used, it is possible to freely set the intensity and the direction of the cancellation magnetic field.

Thus, even in the device employing the electron irradiation system having the objective lens for leaking magnetic field toward the sample side, irradiation to the sample can be obtained without separating the Ga isotope ion beam and it is possible to simultaneously obtain a high micro-machining ability of a particular part of the sample in the FIB machining and a high resolution in the STEM observation in a single sample chamber.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A sample manufacturing method for low energy Scanning Transmission Electron Microscope ("STEM") utilizing a charged particle beam apparatus comprising:
   a low energy electron beam irradiation system for irradiating an electron beam onto a sample while scanning;
   a transmitting electron detector for detecting electrons in an electron beam which has passed through the sample and has scattered at a low scattering angle;
   a scattered electron detector for detecting electrons in an electron beam transmitted and scattered at a large angle by the sample;
   a focused ion beam irradiation system for irradiating a focused ion beam onto the sample while scanning so as to cross-section the sample;
   a secondary electron detector arranged on the same side of the sample as the focused ion beam irradiation system with respect to the sample, the secondary electron detector for detecting secondary electrons emitted from the sample by the beam irradiation of the electron beam or the focused ion beam; and
   a sample holder for holding the sample;
   wherein the irradiation axis of the focused ion beam intersects the irradiation axis of the electron beam almost at a right and fixed angle and the sample holder is arranged on the intersection point of the irradiation axes,
   the method comprising steps of:
   displaying a sample scan image while carrying out focused ion beam cross-sectioning obtained by detecting transmitting and scattering electrons and the secondary electron on an image display means;
   calculating the contrast of the sample scan image obtained by the transmitting and scattering electrons;
   detecting an end point of processing when the contrast becomes saturated and decreases to a preset threshold; and
   stopping the focused ion beam machining when the calculated contrast has reached the preset threshold.

2. The sample manufacturing method for low energy STEM utilizing a charged particle beam apparatus as claimed in claim 1, wherein the low energy electron beam irradiation system has a magnetic field type objective lens and a magnetic field of the objective lens leaks to the position of the sample holder.

3. The sample manufacturing method for low energy STEM utilizing a charged particle beam apparatus as claimed in claim 2, wherein the objective lens is an objective lens of a type forming a magnetic field by a magnetic yoke and the magnetic yoke is arranged only at the electron beam incident side with respect to the sample holder.

4. The sample manufacturing method for low energy STEM utilizing a charged particle beam apparatus as claimed in claim 1, wherein the sample holder has an axis vertical to the irradiation axis of the electron beam and to the irradiation axis of the focused ion beam and is arranged on the axis passing through the intersection point of the two irradiation axes.

5. The sample manufacturing method for low energy STEM utilizing a charged particle beam apparatus as claimed in claim 1, wherein the secondary electron detector has a secondary electron entering plane orthogonally intersecting the plane formed by the irradiation axis of the focused ion beam and the irradiation axis of the electron beam and symmetric with respect to the plane including the irradiation axis of the focused ion beam.

6. The sample manufacturing method for low energy STEM utilizing a charged particle beam apparatus as claimed in claim 1, wherein the image display means displays a sample scan image obtained by the focused ion beam and a sample scan image obtained by the electron beam in a single display frame by separating their areas from each other.

7. The sample manufacturing method for low energy STEM utilizing a charged particle beam apparatus as claimed in claim 6, wherein the image display means displays the contrast of the sample scan image obtained by the electron beam in time series as the sample cross-sectioning advances.

8. The sample manufacturing method for low energy STEM utilizing a charged particle beam apparatus as claimed in claim 7, wherein the charged particle beam apparatus further comprises:
   a register for registering a threshold of the brightness, the contrast, the S/N ratio, or the image resolution; and
   a controller for controlling irradiation of the focused ion beam;
   wherein the controller stops irradiation of the focused ion beam when the contrast by the electron bean has reached the threshold registered by the register.

9. A sample manufacturing method for low energy Scanning Transmission Electron Microscope ("STEM") utilizing a charged particle beam apparatus comprising:
   a low energy electron beam irradiation system for irradiating an electron beam onto a sample while scanning;
   a detector for detecting electrons in an electron beam which passed through the sample and scattered at a low angle and electrons in an electron beam transmitted and scattered at a large angle by the sample;
   a focused ion beam irradiation system for irradiating a focused ion beam onto the sample while scanning so as to cross-section the sample; and
   a secondary electron detector arranged on the same side of the sample as the focused ion beam irradiation system with respect to the sample, the secondary electron detector for detecting secondary electrons emitted from the sample by the beam irradiation of the electron beam or the focused ion beam;
   the method comprising steps of:
   while carrying out focused ion beam cross-sectioning, displaying a sample scan image obtained by detection of transmitting and scattering electrons and the secondary electron, on an image display;
   calculating the contrast of the sample scan image obtained by the transmitting and scattering electrons;
   detecting an end point of processing when the contrast becomes saturated and decreases to a preset threshold; and stopping the focused ion beam machining when the calculated contrast has reached a preset threshold.

10. The sample manufacturing method for low energy STEM utilizing a charged particle beam apparatus as claimed in claim 1, wherein the focused ion beam is configured to perform cross-sectional processing to the sample.

11. The sample manufacturing method for low energy STEM utilizing a charged particle beam apparatus as claimed in claim 9, wherein the focused ion beam is configured to perform cross-sectional processing to the sample.

12. The sample manufacturing method for low energy STEM utilizing a charged particle beam apparatus as claimed in claim 1, wherein an electron beam which passed through the sample and scattered at a low scattering angle and an electron beam transmitted and scattered at a large angle by the sample are directly detected, and a dark field imaging and bright field imaging, respectively, are carried out.

13. The sample manufacturing method for low energy STEM imaging method utilizing a charged particle beam apparatus as claimed in claim 9, wherein an electron beam which passed through the sample and scattered at a low scattering angle and an electron beam transmitted and scattered at a large angle by the sample are directly detected, and a dark field imaging and bright field imaging, respectively, are carried out.

* * * * *